(12) United States Patent
Hurtevent et al.

(10) Patent No.: US 10,989,665 B2
(45) Date of Patent: Apr. 27, 2021

(54) METHOD AND SOLUTION FOR ASSAYING INHIBITORS IN A PETROLEUM FLUID CONTAINING WATER

(71) Applicants: TOTAL SA, Courbevoie (FR); UNIVERSITE CLAUDE BERNARD LYON 1, Villeurbanne (FR); CENTRE NATIONAL DE LA RECHERCHE SCIENTIFIQUE, Paris (FR)

(72) Inventors: Christian Hurtevent, Saint Chamarand (FR); Salima Baraka-Lokmane, Pau (FR); Olivier Tillement, Fontaines Saint-Martin (FR); Arthur Marais, Lochrist (FR); Mattéo Martini, Lyons (FR); Mahmoud Ould-Metidji, Lyons (FR); Francisco Vasquez Velado, Lyons (FR); Florian Lepoivre, Lyons (FR)

(73) Assignees: TOTAL SA, Courbevoie (FR); UNIVERSITE CLAUDE BERNARD LYON 1 (UCBL), Villeurbanne (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 456 days.

(21) Appl. No.: 15/737,534

(22) PCT Filed: Jun. 17, 2015

(86) PCT No.: PCT/FR2015/051608
§ 371 (c)(1),
(2) Date: Dec. 18, 2017

(87) PCT Pub. No.: WO2016/203119
PCT Pub. Date: Dec. 22, 2016

(65) Prior Publication Data
US 2018/0172596 A1 Jun. 21, 2018

(51) Int. Cl.
*G01N 21/77* (2006.01)
*G01N 21/64* (2006.01)
(Continued)

(52) U.S. Cl.
CPC ............. *G01N 21/77* (2013.01); *C09K 8/528* (2013.01); *G01N 21/643* (2013.01);
(Continued)

(58) Field of Classification Search
CPC .. G01N 21/77; G01N 33/2835; G01N 21/643; G01N 21/6408; G01N 31/22; G01N 2021/7786; C09K 8/528; C09K 2208/32
(Continued)

(56) References Cited

U.S. PATENT DOCUMENTS 5,316,909 A * 5/1994 Xu ..................... G01N 33/582
435/6.12
5,622,821 A * 4/1997 Selvin ................. G01N 33/533
435/6.11
(Continued)

FOREIGN PATENT DOCUMENTS

| WO | 2015/075300 A1 | 5/2015 |
| WO | 2015/075309 A1 | 5/2015 |
| WO | 2015/092310 A1 | 6/2015 |

OTHER PUBLICATIONS

Martini et al. "How to Monitor Scale Inhibitor Squeeze Using Simple TRF Tracers" SPE-173768-MS 2015 (Year: 2015).*
(Continued)

*Primary Examiner* — Samuel P Siefke
(74) *Attorney, Agent, or Firm* — Oliff PLC (57) ABSTRACT

A method for detecting and quantifying additives in a complex aqueous fluid, and a method for detecting an inhibitor of mineral deposition or corrosion, injected in a gas or oil well. The invention also relates to a developer solution
(Continued)

including a lanthanide and a chelating agent for detecting said additives or inhibitors.

16 Claims, 10 Drawing Sheets

(51) Int. Cl.
*C09K 8/528* (2006.01)
*G01N 33/28* (2006.01)
*G01N 31/22* (2006.01)

(52) U.S. Cl.
CPC ..... *G01N 21/6408* (2013.01); *G01N 33/2835* (2013.01); *C09K 2208/32* (2013.01); *G01N 31/22* (2013.01); *G01N 2021/7786* (2013.01)

(58) Field of Classification Search
USPC .......................................................... 436/81
See application file for complete search history.

(56) References Cited

U.S. PATENT DOCUMENTS

2004/0082768 A1    4/2004  Murthy et al.
2011/0177534 A1*   7/2011  Salant ................ G01N 33/564
                                                                    435/7.92

OTHER PUBLICATIONS

Thomas Brichart et al., "Use of Fluorescent Tracers for Inhibitor Concentration Monitoring Useful for Scale Inhibitor Squeeze Evaluation", Dec. 10, 2014, url:https://www/onepetro.org/conference/SPE/150CS.

James Johnstone et al., "Novel Method for Real-Time Monitoring of Scale Control Products at the Site of Use", May 14, 2014, pp. 14-15, url: https://www.onepetro.org/conference/SPE/140SS.

William Dew Horrocks Jr. et al., "Lanthanide Ion Probes of Structure in Biology. Laser-Induced Luminescence Decay Constants Provide a Direct Measure of the Number of Metal-Coordinated Water Molecules", Journal of the American Chemical Society, vol. 101, No. 2, Jan. 17, 1979, pp. 334.

L. Armelao et al., "Design of Luminescent Lanthanide Complexes: From Molecules to Highly Efficient Photo-Emitting Materials", Coordination Chemistry Reviews, vol. 254, (2010), pp. 487-505.

Eva F. Gudgin Dickson et al., "Ultrasensitive Bioanalytical Assays Using Time-Resolved Fuorescence Detection", Pharmacol. Ther., vol. 66, No. 2, pp. 207-235, 1995.

Mar. 29, 2016 Search Report issued in International Patent Application No. PCT/FR2015/051608.

* cited by examiner

Figure 8 (a) and (b)

METHOD AND SOLUTION FOR ASSAYING INHIBITORS IN A PETROLEUM FLUID CONTAINING WATER

TECHNICAL FIELD

The present invention relates to a method for detecting and quantifying additives in a complex aqueous fluid, and in particular a method for detecting an inhibitor of mineral deposits or of corrosion that is injected into a gas or oil well. It also relates to a developing solution comprising a lanthanide and a chelating agent for detecting said additives or inhibitors.

BACKGROUND OF THE INVENTION

During exploitation of oil or gas fields, the recovery of gas or oil can be improved by injecting water into the deposit, via an injection well, so as to force the oil of the deposit out of the subsoil, via at least one other well, called a producing well. The interaction of the injected water with the reservoir containing gas, oil and underground water can lead to the formation of chemical species that can cause faults in the operation of the facility. More particularly, deposits of barium sulphate, calcium carbonate or sulphides of zinc and lead, for example, are in particular likely to be formed under conditions of exploitation at high pressure and high temperature or when the brine injected for extracting the oil or gas comes into contact with hydrogen sulphide or the ions contained in the reservoir. The production of reservoir water or aquifer water simultaneously with the oil or gas can lead to the same phenomena. These mineral deposits can obstruct the flow channels in the formation, contaminate the pipelines and the surface equipment and block the pumping systems.

More generally, mineral deposits or corrosion phenomena can appear under various operating conditions of industrial installations in contact with an aqueous environment.

In order to prevent or slow down these phenomena, additives are injected, for example into the underground formation or in the gas or oil wells. An example of such additives is constituted by inhibitors of mineral deposits and corrosion inhibitors. The injection of a fluid containing an inhibitor capable of preventing the formation of the crystals that cause the problems, of preventing their growth or dispersing them, thus makes it possible to overcome the aforementioned drawbacks and avoid or delay dismantling the installations in order to clean them.

However, assay (detection and/or quantification) of these inhibitors constitutes an essential aspect of the production of hydrocarbons, in order to ensure that they are present in sufficient quantity to fulfil their function with, if necessary, timely injection of an additional quantity of inhibitor, adjusted to take account of the economic constraints of the process and its environmental impact.

The methods currently used for determining these inhibitors are often of low accuracy and/or take a long time and require equipment that is often rather unsuitable for the exploitation conditions. An example of these methods is the determination of corrosion inhibitors using methyl orange. Although this technique is extremely flexible, it sorely lacks reliability and has a very high relative uncertainty as regards the results.

Determination of molecules that inhibit mineral deposits requires accurate chemical analysis for a certain number of specific elements of one of the molecules used (measurement of the level of nitrogen or of phosphorus for example, the so-called Hyamine method for polymers). These measurements can be carried out either by mass spectrometry and/or by separation and concentration using analytical devices such as high-performance liquid chromatography (HPLC). These techniques are both complex and difficult to implement.

Moreover, development of a detection method that is reliable and rapid comes up against the fact that these additives or inhibitors are generally so effective that they are only present in the injected fluid at the level of a few ppm, and that the fluid constituted by the exploitation waters contains a variety of compounds such as salts and organic residues. Owing to the presence of these compounds, the complex fluid produced in particular has an intrinsic fluorescence that prevents detection of additives or inhibitors, optionally labelled with a fluorescent probe, using traditional fluorescence techniques. Finally, the production sites are generally located in remote places, far from local analytical laboratories, which represent an additional constraint.

It would therefore be desirable to be able to determine these additives or inhibitors directly on site, in the production waters, using a method that is simple, reliable and accurate, that can be used for a variety of inhibitors of mineral deposits and corrosion inhibitors and that can be carried out using easily transported, compact equipment.

The inventors demonstrated that these requirements could be satisfied by mixing the fluids to be analysed, which may contain these additives, with a developing solution comprising at least one lanthanide ion and at least one chelating agent of the lanthanide ion and using the time-resolved fluorescence method. This method in fact makes it unnecessary to employ the natural fluorescence of the exploitation water, which has very short emission times, and only collect the light emitted after a delay a few microseconds to one millisecond, preferably from 100 microseconds to one millisecond, resulting from the fluorescence of the inhibitors labelled in this way. Furthermore, pre-complexation of the lanthanide ions with a chelating agent makes it possible to considerably improve the sensitivity of detection of the additives or inhibitors, even despite the increase in fluorescence of the lanthanide ions associated with the presence of the chelating agent. The present method also makes it possible to detect additives or inhibitors with low complexing power (in particular certain amine-containing corrosion inhibitors) or that are easily excitable in the near UV/visible (such as europium).

This method has the further advantage of specifically identifying the type of additive, for example inhibitor (of mineral deposits or of corrosion), without a preliminary labelling step and even when it is present in a complex fluid formed by the production water in the petroleum medium, as a function of its optical signature, simultaneously employing the excitation and emission spectra and the lifetimes of the signals emitted.

SUMMARY OF THE INVENTION

The present invention relates to a method for detecting additives in an aqueous fluid, comprising:
  a. mixing a developing solution comprising a lanthanide cation and a lanthanide chelating agent, with a sample of the aqueous fluid to be analysed optionally comprising at least one additive, under conditions allowing complexing of the lanthanide by the chelating agent and by the additive that is optionally present, b. detecting and, if appropriate, quantifying the variation in fluorescence associated with the possible presence of the additive in the aqueous fluid by time-resolved fluorescence.

It also relates to a developing solution for detecting additives and in particular inhibitors of mineral deposits or of corrosion, comprising:
(i) a lanthanide cation, for example Eu3+,
(ii) a lanthanide chelating agent, for example selected from diaminopyridine, imidazoline, hydrolysed poly(maleic anhydride), polycarboxylics, oxalic acid, acetylacetonate, thiodiacetate, or derivatives thereof, EDTA, nitrilotriacetic acid (NTA);
(iii) chloride ions at more than 1 g/L;
(iv) if appropriate, a chemical compound used in the production of buffer solution at more than 1 g/L, for example HEPES;
the concentration ratio of the chelating agent to the lanthanide being comprised between 1:10 and 10:1, preferably between 1:3 and 3:1.

DETAILED DESCRIPTION OF EMBODIMENTS

The method according to the invention essentially comprises:
mixing a developing solution comprising a lanthanide cation and a lanthanide chelating agent, with a sample of the aqueous fluid to be analysed optionally comprising at least one additive, under conditions allowing complexing of the lanthanide by the chelating agent and by the additive, and
detecting and, if appropriate, quantifying the variation in fluorescence associated with the possible presence of the additive in the aqueous fluid by time-resolved fluorescence.

Developing Solution for Carrying Out the Method for Detecting Additives

Implementation of the detection method comprises the use of a developing solution comprising at least one lanthanide cation and at least one lanthanide chelating agent.

By "lanthanide chelating agent" is meant an ion or a molecule bearing chemical functions allowing it to bind to one or more central atoms or ions of said lanthanide and for which the lanthanide/ligand interaction thus formed is greater than the lanthanide/water interaction and preferably greater than the lanthanide/chloride interaction, thus allowing pre-complexing of the lanthanide ions by reducing the number of water molecules present in the coordination sphere of the lanthanide, resulting in a decrease in the quenching effect of the water on the fluorescence of the lanthanide ion (W. D. Horrocks et al., JACS 1979 101:2, 334-340).

The chelating agents of the lanthanides usable in the developing solution are preferably selected from:
(i) the molecules comprising at least one amine function, preferably two amine functions, and/or
(ii) the molecules comprising at least one carboxylic acid function, in particular maleic acid or polymeric derivatives of maleic acid.

In a specific embodiment, the chelating agent further comprises at least one aryl group, preferably a single heterocyclic group, substituted or unsubstituted, for example a pyridine group and substituted derivatives thereof. Besides the chelating effect provided by the amine or carboxylic acid function, the presence of an aryl group and for example a pyridine group additionally allows amplification of the fluorescence signal by the antenna effect (Armelao, L.; et al. COORDINATION CHEMISTRY REVIEWS Volume: 254 Issue: 5-6 Special Issue: SI Pages: 487-505 Published: MARCH 2010).

In a preferred embodiment, the chelating agent is selected from diaminopyridine, imidazoline, hydrolysed poly(maleic anhydride), the polycarboxylic acids, EDTA, oxalic acid, acetylacetonate, thiodiacetate, nitrilotriacetic acid (NTA), derivatives thereof or mixtures thereof.

In a specific embodiment, the developing solution further comprises at least 1 g/L of chloride ions, and preferably a concentration of chloride ions between 10 and 50 g/L.

In another particular embodiment that may be combined with the preceding embodiments, the developing solution further comprises at least 1 g/L of a compound with a high buffer capacity, used in the production of buffer solution, and allowing the pH value to be maintained after adding 1/10 of water to be analysed in a pH range below 0.5 unit, for example 4-(2-hydroxyethyl)-1-piperazine-ethanesulphonic acid (HEPES).

The concentration ratio of the chelating agent to the lanthanide in the developing solution is comprised between 1:10 and 10:1, for example between 1:3 and 3:1.

The lanthanide cation usable in the developing solution can be selected from the elements from atomic number 57 (lanthanum) to 71 (lutetium), such as Pr, Nd, Sm, Eu, Tb, Dy, Ho, Er, Tm and Yb, and mixtures thereof. The present method is particularly suitable for a developing solution comprising europium, fluorescence variations of which are more difficult to detect in the absence of the chelating agent present in the developing solution. Advantageously, the fluorescence emitted by europium can be measured by means of disposable plastic cells, without the need to use cells that are transparent in the UV (such as cells made of quartz or silica).

The invention relates in particular to a developing solution for detecting additives and in particular inhibitors of mineral deposits or of corrosion, comprising:
i. a lanthanide cation, for example Eu3+,
ii. a lanthanide chelating agent, for example selected from diaminopyridine, imidazoline, hydrolysed poly(maleic anhydride), the polycarboxylic acids, oxalic acid, acetylacetonate, thiodiacetate, or derivatives thereof, EDTA, nitrilotriacetic acid (NTA);
iii. chloride ions at more than 1 g/L;
iv. if appropriate, a chemical compound used conventionally in the production of buffer solutions, for example 4 (2-hydroxyethyl)-1-piperazine-ethanesulphonic acid (HEPES) at more than 1 g/L, for example HEPES: 4-(2-hydroxyethyl)-1-piperazine-ethanesulphonic acid;
the concentration ratio of the chelating agent to the lanthanide being comprised between 1:10 and 10:1, preferably between 1:3 and 3:1.

In a particular embodiment, the developing solution comprises between 10 and 1000 ppm of $EuCl_3 \cdot 6H_2O$, 10 and 5000 ppm of imidazoline and between 5 and 50 g/L of NaCl, at a pH comprised between 4 and 8.

In another embodiment, the developing solution comprises between 1 and 100 ppm of $EuCl_3 \cdot 6H_2O$, 2 and 200 ppm of hydrolysed poly(maleic anhydride) and between 5 and 50 g/L of NaCl, at a pH comprised between 4 and 8.

The present invention relates to the developing solutions as defined above as such, the preparation methods thereof, and the uses thereof in a method for detecting additives as defined below.

Aqueous Fluid to be Analysed, Extraction and Mixing with the Developing Solution The method for detecting additives comprises extracting a sample (aqueous fluid) to be analysed and mixing it with the developing solution defined above.

The additives that may be present in the sample to be analysed, and are detectable by the detection method according to the invention, are in particular those having at least one amine function.

In an embodiment, the additive does not have intrinsic fluorescence. Advantageously, with the method according to the present invention, the additive to be detected has not been coupled to a chelating agent prior to its injection or a luminescent agent or other labelling agent.

The method can therefore be applied for example to the analysis and detection of chemical additives used in the chemical industry or present in the environment.

Preferably, the method relates to the detection of inhibitors of mineral deposits or of corrosion, in particular in an extract of a petroleum fluid containing water, for example an extract from a producing well for oil or gas. In a preferred embodiment of the method according to the invention, a sample of aqueous fluid to be analysed is extracted from a producing well for oil or gas or from industrial water taken during exploitation and/or production.

By "inhibitor of mineral deposits" is meant a compound capable of preventing or slowing down the formation (i.e. nucleation and/or growth) of crystals of mineral salts in particular selected from: calcium carbonate, calcium sulphate, barium sulphate, strontium sulphate, the sulphides of zinc, of lead and of iron and mixtures thereof. The inhibitors of mineral deposits detectable by the method of the invention are in particular:

polyphosphates, such as sodium tripolyphosphate (STPP), sodium hexametaphosphate (SHMP), organophosphonates, such as amino tri(methylene phosphonic) acid or AMP, 1-hydroxyethylidene-1,1-diphosphonic acid or HEDP, ethylenediamine tetra(methylene phosphonic) acid or EDTMP, hexamethylenediamine tetra(methyl phosphonic) acid or HMTMP, diethylenetriamine penta(methylene phosphonic) acid or DETMP, hydroxyethylamino-di(methylenephosphonic) acid (HEMPA), polycarboxylic acids such as 2-phosphonobutane 1,2,4-tricarboxylic acid or PBTC, poly(acrylic acid) or PAA, poly(methacrylic acid) or PMAA, poly(maleic acid) or PMA, polymers with a sulphonic acid function, such as copolymers of styrenesulphonic acid and polycarboxylic acid, in particular copolymers of styrenesulphonic acid and maleic acid, copolymers of styrenesulphonic acid and (poly)amido-amine, homo- and copolymers of vinyl sulphonate, in particular copolymers of vinyl sulphonate, styrene and maleic anhydride, alkyldiphenyl ether sulphonates and copolymers of acrylamidomethylpropane sulphonic acid (AMPS), maleic acid and acrylic acid, polyphosphinocarboxylic acid (PPCA), optionally sulphonated, polyethyleneimine (PEI), silicone polymers, in particular polydimethylsiloxanes, functionalized with amine groups, and copolymers based on quaternary ammonium, such as the copolymers of acrylamide, quaternary ammonium and optionally acrylate, the copolymers of acrylamide, diallyldimethylammonium salt and optionally acrylate.

By "corrosion inhibitor" is meant a compound capable of reducing the rate of corrosion of a material, typically a metal or a metal alloy, due to the action of an oxidant such as dioxygen or $H^+$ ion on this material. Examples of corrosion inhibitors are in particular mono-, di- and triamines such as cyclohexylamine, hexylamine, morpholine, imidazoline or octadecylamine, as well as amino alcohols such as diethylaminoethanol, quaternary ammoniums and betaines.

In the method according to the invention, the volume extracted from the sample to be analysed (for example extracted from an oil or gas well) can be for example comprised between 0.1 mL and 1 litre, 5 litres, 10 litres or more.

The volume extracted can be treated before analysis, for example by acid/base/oxidation/precipitation or by steps of filtration or sedimentation in order to remove certain undesirable compounds, before mixing with the developing solution.

This sample (for example extracted from an oil or gas well) is mixed with the developing solution, for example at ratios from 1:100 to 100:1 v/v of the volume of the sample to be analysed to the volume of developing solution, and preferably comprised between 1:20 and 1:5, for example around 1:10.

The lanthanide ions pre-complexed with the chelating agents present in the developing solution form complexes with any additives present in the sample (for example inhibitors of deposits or of corrosion). This results in a decrease in the quenching effect of the water molecules around the lanthanide cations and therefore an increase in fluorescence of the lanthanide cations.

Detection of Additives in the Sample to be Analysed

For the detection of additives in the sample to be analysed with the method according to the invention, the variation in fluorescence between this mixture comprising lanthanide ions optionally complexed with an additive and a control mixture (for example not containing an additive or containing a known quantity of an additive) is measured by time-resolved fluorescence.

Due to the decrease in the quenching effect of water on the lanthanide in the presence of the additive, the variation in fluorescence relative to a reference solution without the additive (or with a known quantity of the additive) is thus related directly and specifically to the presence of the additive in the fluid to be analysed.

Comparison of the characteristics of emission, excitation and/or lifetime of the free lanthanide ions and complexed lanthanide ions thus makes it possible to detect and, if appropriate, quantify the inhibitors present in the fluid extracted.

According to the invention, the additive (for example the inhibitor of deposits or of corrosion) is detected, and the level thereof is quantified, using a time-resolved fluorescence technique, which is in particular described in the article "Ultrasensitive bioanalytical assays using time resolved fluorescence detection", *Pharmacol. Ther.* Vol. 66(2), pp. 207-35, 1995. This is based on the application of a delay, called the integration delay, between excitation of the sample to be analysed and measurement of the signal emitted, so as to avoid short-lived parasitic fluorescence. This method can be implemented at ambient temperature, in particular using equipment of the Cary Eclipse type from the company Agilent.

The excitation wavelength can be comprised between 200 and 600 nm and the emission wavelength can be comprised between 300 and 800 nm. The integration delay can be comprised between 0.001 and 10 ms, preferably between 0.01 and 5 ms, more preferably between 0.1 and 3 ms. In certain cases, the longer this delay, the better the signal/noise ratio, which improves the reliability of measurement. The time for collecting the photons can be from 5 to 10 ms, for example.

This method can be applied in various ways. Thus, it is possible to compare the intensity of emission from the sample tested with those obtained at different concentrations of inhibitor, and deduce from that the concentration of the inhibitor in the sample. As a variant, it is possible to detect several inhibitors in the test sample by measuring the rate of decrease of the signal emitted by the sample, or half-life, and by comparing the values obtained with those known for the various additives to be detected.

The present invention will be better understood in light of the following non-limitive examples, which are given purely by way of illustration and are not intended to limit the scope of this invention, which is defined by the attached claims.

EXAMPLES

I-Preparation of Solutions of Additives and of the Developing Solutions
Preparation of the Saline Water:
Synthetic Water (Sample 1)

TABLE 1

| saline composition of the synthetic water (sample 1) | |
|---|---|
| | Sample 1 (g/L) |
| NaCl | 96.00 |
| $CaCl_2$ | 134.65 |
| $MgCl_2 \cdot 6H_2O$ | 26.40 |
| KCl | 5.70 |
| $BaCl_2 \cdot 2H_2O$ | 0.55 |
| $SrCl_2 \cdot 6H_2O$ | 1.90 |

TABLE 2

| Composition of the synthetic water (sample 2) | |
|---|---|
| | Sample 2 (g/L) |
| NaCl | 90.44 |
| $CaCl_2$ | 18.66 |
| $MgCl_2 \cdot 6H_2O$ | 1.08 |
| KCl | 10.59 |
| $BaCl_2 \cdot 2H_2O$ | 2.47 |
| $SrCl_2 \cdot 6H_2O$ | 2.24 |

Preparation of a Stock Solution of Europium:
250 mg of europium trichloride hexahydrate (CAS: 13759-92-7; $EuCl_3 \cdot 6H_2O$) is weighed in a 500-mL flask. Then 500 mL of ultra-pure water is added. The sample is stirred for approximately 1 h. A solution of $EuCl_3 \cdot 6H_2O$ at 500 ppm is obtained.

Preparation of a Stock Solution of HEPES (Buffer):
2.98 g of HEPES (CAS: 7365-45-9; C8H18N2O4S; Sigma Aldrich) is weighed in a 250-mL flask. Then 250 mL of ultra-pure water is added. The sample is stirred for approximately 1 h. A solution of HEPES at 11.92 g/L is obtained.

Preparation of a Stock Solution of Diamino Amplifying Chelating Agents (DAP)
1 g of 2,5-diaminopyridine dihydrochloride (DAP) (CAS: 26878-35-3; C5H7N3.2HCl; Alfa Aesar) is weighed in a 100-mL flask. Then 100 mL of ultra-pure water is added. The sample is stirred for approximately 1 h. A red solution with 10 g/L of DAP is obtained.

Preparation of a Stock Solution of Carboxylated Amplifying Chelating Agents (F110)
200 mg of the sodium salt of poly(4-styrenesulphonic acid, co-maleic acid) (CAS: 68037-40-1; [CH2CH (C6H4SO3R)]×[CH(CO2R)CH(CO2R)]y R=H/Na; Sigma Aldrich) is weighed in a 100-mL flask. Then 100 mL of ultra-pure water is added. The sample is stirred for approximately 1 h. A solution of complexing agent at 2 g/L is obtained.

Preparation of a Reference Solution of Nalco EC1621A Corrosion Inhibitor
1 g of Nalco EC1621A solution (manufactured by Nalco, Ecolab Europe GmbH Switzerland) is weighed in a 100-mL flask. Then 100 mL of ultra-pure water is added. The sample is stirred for approximately 1 h. A solution of Nalco EC1621A at 10 g/L is obtained.

Preparation of a Reference Solution of Norust 9711 Corrosion Inhibitor
1 g of Norust 9711 solution (manufactured by CECA, Groupe Arkema France) is weighed in a 100-mL flask. Then 100 mL of ultra-pure water is added. The sample is stirred for approximately 1 h. A solution of Norust 9711 at 10 g/L is obtained.

Preparation of the Eu-Light Developing Solution Without Chelating Agent
25 mL of the Hepes stock solution is placed in a 500-mL flask. Then 50 mL of the stock solution is added with 425 mL of ultra-pure water and 10 g of sodium chloride. The pH is then adjusted to 6.5 with a 1M NaOH solution. A developing solution at pH 6.5 with 25 ppm of $EuCl_3 \cdot 6H_2O$ and 20 g/L of NaCl is obtained.

Preparation of a Solution of Gyptron SA3470 Corrosion Inhibitor in Saline Water (Solution TEST1)
1 g of the commercial solution of Gyptron SA3470 (manufactured by Champion Technologies Ltd, UK) is weighed in a 100-mL flask. Then 100 mL of saline water (synthetic water, sample 1) is added. The sample is stirred for approximately 1 h. 5 mL of the solution prepared is taken and then placed in a 500-mL flask. Finally, 495 mL of saline water (synthetic water, sample 1) is added. A solution with 100 ppm of commercial solution of Gyptron SA3470 in synthetic saline water is obtained (sample 1).

Preparation of a Solution of Deposit Inhibitor F11 in Saline Water (Solution TEST2)

1 g of deposit inhibitor F11 is weighed in a 100-mL flask. Then 100 mL of saline water (synthetic water, sample 2) is added. The sample is stirred for approximately 1 h. 5 mL of the solution prepared is taken and then placed in a 500-mL flask. Finally, 495 mL of synthetic saline water sample 2 is added. A solution with 100 ppm of F11 in saline water is obtained.

Preparation of a Solution of Deposit Inhibitor ZFD in Saline Water (Solution TEST3)

1 g of ZFD is weighed in a 100-mL flask. Then 100 mL of saline water (synthetic water, sample 2) is added. The sample is stirred for approximately 1 h. 5 mL of the solution prepared is taken and then placed in a 500-mL flask. Finally, 495 mL of synthetic saline water (sample 2) is added. A solution with 100 ppm of ZFD in saline water is obtained.

Preparation of a Solution of Nalco EC1621A Corrosion Inhibitor in Saline Water (Solution TEST4)

1 mL of the reference solution with Nalco EC1621A is placed in a 100-mL flask. Then 99 mL of synthetic saline water (sample 2) is added. A solution with 100 ppm of Nalco EC1621A in saline water is obtained.

Preparation of a Solution of Norust 9711 Corrosion Inhibitor in Saline Water 1 mL of the reference solution with Norust 9711 is put in a 100-mL flask. 99 mL of saline water (synthetic water, sample 2) is added. A solution with 100 ppm of Norust 9711 in saline water is obtained.

Example 1

Preparation of the Developing Solution Amplified with the Imidazoline Pre-Complexing Agent: Eu-IM25100

For a solution at 25 ppm of europium salt (Eu-IM25100): 25 mL of the stock solution of europium is placed in a 500-mL flask. Then 50 mL of the stock solution of HEPES as well as 420 mL of ultra-pure water is added. 5 mL of a solution at 10 g/L of a commercial solution of imidazoline and 10 g of sodium chloride are then added. The pH is then adjusted to 6.5 with a 1M NaOH solution. A developing solution at pH 6.5 with 25 ppm of $EuCl_3.6H_2O$, 100 ppm of a commercial solution of imidazoline and 20 g/L of NaCl is obtained.

Example 2

Preparation of the Developing Solution Amplified with the Diamino Pre-Complexing Agent (DAP): Eu-LD20

The quantity of europium salt is adjusted according to the desired concentration. For a solution with 5 ppm of europium salt (Eu-LD520): 5 mL of the europium stock solution is placed in a 500-mL flask. Then 50 mL of the HEPES stock solution as well as 444 mL of ultra-pure water are added. 1 mL of the stock solution of DAP chelating agent and 10 g of sodium chloride are then added. The pH is then adjusted to 6.5 with a 1M NaOH solution. A developing solution at pH 6.5 with 5 ppm of $EuCl_3.6H_2O$, 20 ppm of DAP and 20 g/L of NaCl is obtained.

Example 3

Preparation of the Detecting Solution Amplified with the Carboxylated Pre-Complexing Agent: Eu-F110

The quantity of europium salt is adjusted according to the desired concentration. For a solution with 5 ppm of europium salt (Eu-FL510): 5 mL of the europium stock solution is placed in a 500-mL flask. Then 50 mL of the HEPES stock solution as well as 442.5 mL of ultra-pure water are added. Finally, 2.5 mL of the stock solution of F110 and 10 g of sodium chloride are added. The pH is then adjusted to 6.5 with a 1M NaOH solution.

A developing solution at pH 6.5 with 5 ppm of $EuCl_3.6H_2O$, 10 ppm of carboxylated pre-complexing agent and 20 g/L of NaCl is obtained.

II-Methods for Quantifying the Additives

Figure 1:
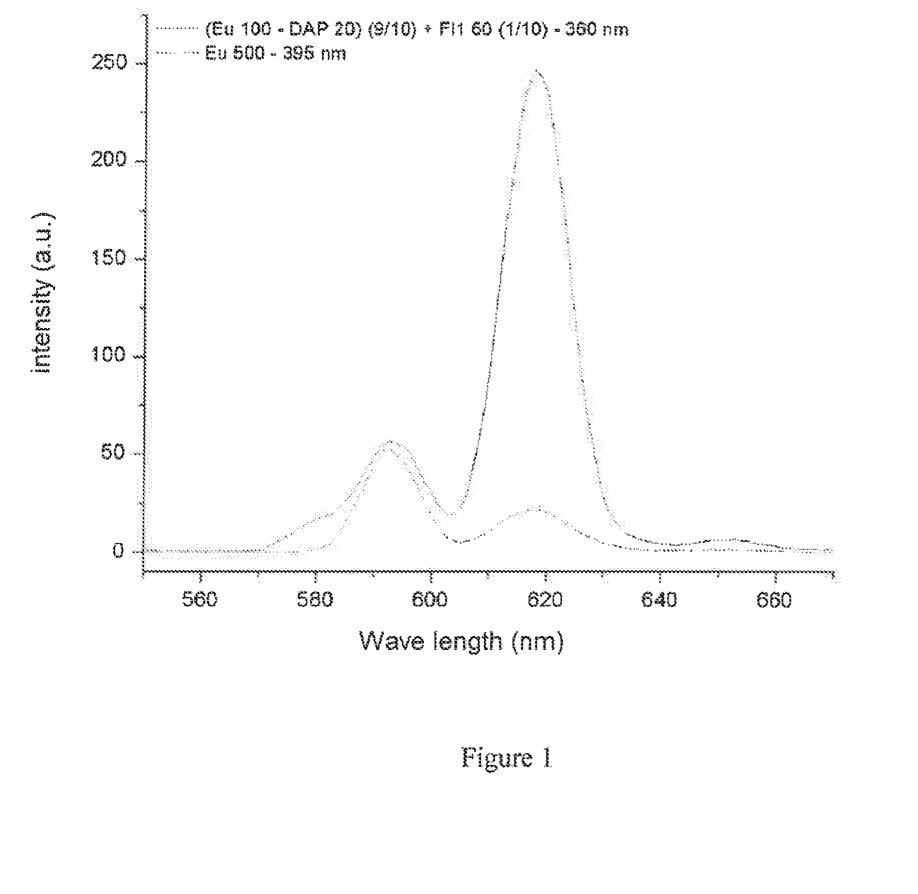
FIG. 1 shows an emission spectrum of free europium (bottom curve, Eu 500-395 nm) and of europium complexed with FL1/DAP (top curve) (Eu 100-DAP 20) (9/10) and FL1 60 (1/10)-360 nm.

Quantification of the Additives by Time-Resolved Fluorescence (TRF):

The measurements are carried out on an Agilent Cary Eclipse spectrofluorometer. They are carried out in 4-mL PMMA cuvettes (reference). The concentrations of developing solutions are fixed for decreasing concentrations of formulated additive, synthetic water sample 1. The luminescence lifetime of the rare earths increases with the decrease in the number of water molecules in their coordination sphere. Complexing of the rare earths with additives such as inhibitors thus allows them to be detected and quantified. This complexing is characterized by an increase in intensity of emission and inversion of the ratio of the peaks I595nm/I615nm (FIG. 1).

The fluorescence lifetimes of these complexes are typically of the order of a millisecond. This property in particular makes it possible to distinguish them from the fluorescence of the organic compounds, which is of the order of a microsecond.

The europium complexes have four notable peaks in the visible range: 536, 595, 614 and 650 nm. The limits of the equipment (loss of sensitivity for λem>600 nm) led us to quantify these entities via the emission at 614 nm. The intensity of the peak is related to the concentration, the degree of complexing and the detection conditions.

Assay by TRF with the Eu-Light Europium Developing Solution

The excitation and emission wavelengths are set at 395 nm and 617 nm respectively. The delay time is set at 0.2 ms and the gate time at 1 ms.

Assay by TRF with the Developing Solution Eu-IM25100 (Example 1) and Eu-LD20 (Example 2)

The excitation and emission wavelengths are set at 360 nm and 617 nm respectively. The delay time is set at 0.2 ms and the gate time at 1 ms.

Assay by TRF with the Developing Solution Eu-F110 (Example 3)

The excitation and emission wavelengths are set at 350 nm and 617 nm respectively. The delay time is set at 0.1 ms and the gate time at 1 ms.

II-1 Detection of the Deposit Inhibitors

TEST 1: Procedure for Quantifying Gyptron SA3470

Several samples are prepared from the solution TEST1 in order to obtain a concentration range between 0 and 100 ppm in sample 1. These samples are assayed by TRF according to 2 methods:

1 mL of each sample is placed in 10-mL flasks in the presence of 9 mL of the Eu-light solution (europium only). After one hour, 2 mL of these new solutions is analysed according to the experimental conditions defined above.

1 mL of each sample is placed in 10-mL flasks in the presence of 9 mL of the solution from Example 2.

After one hour, 2 mL of these new solutions is analysed according to the experimental conditions defined above.

Figure 2:
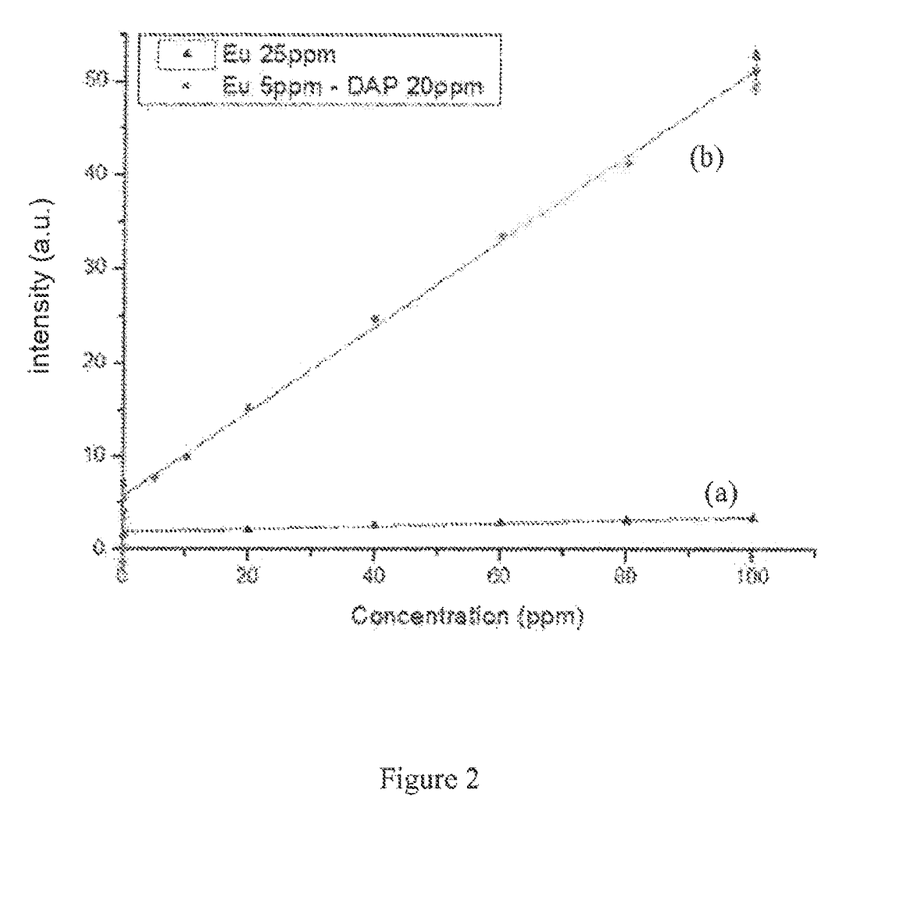
FIG. 2 shows a calibration curve of Gyptron SA3470 by europium with (a) the solution Eu-Light ($\lambda_{exc}$=395 nm) and (b) Eu-LD520 ($\lambda_{exc}$=360 nm).

The calibration curves obtained are presented in FIG. 2. When the method is used, the straight lines show an effect of enhancement of the fluorescence accompanied by an increase in measurement sensitivity while maintaining linearity.

TEST2: Procedure for Quantifying F11

Several samples are prepared from the solution TEST2 in order to obtain a concentration range between 0 and 100 ppm in synthetic saline water (sample 2). These samples are assayed by TRF according to 2 methods:

1 mL of each sample is placed in 10-mL flasks in the presence of 9 mL of the Eu-Light solution (europium only). After one hour, 2 mL of these new solutions is analysed according to the conditions defined above.

1 mL of each sample is placed in 10-mL flasks in the presence of 9 mL of the solution from Example 1. After one hour, 2 mL of these new solutions is analysed according to the experimental conditions defined above.

0.5 mL of each sample is placed in 10-mL flasks in the presence of 9.5 mL of the solution from Example 2. After one hour, 2 mL of these new solutions is analysed according to the experimental conditions defined above.

Figure 3:
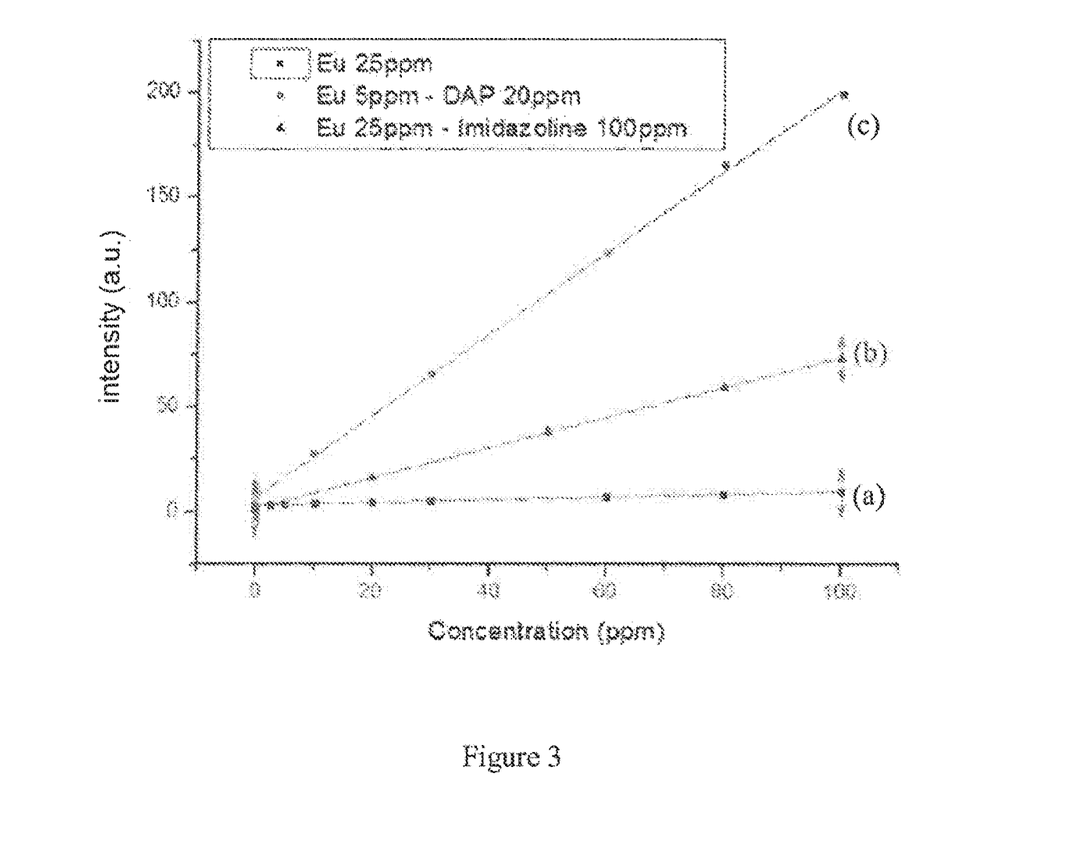
FIG. 3 shows the calibration curves of F11 by europium (a) Eu-light ($\lambda_{exc}$=395 nm), (b) Eu—IM25100 ($\lambda_{exc}$=360 nm).

The calibration curves obtained are presented in FIG. 3. When the method is used, the straight lines show an effect of enhancement of the fluorescence accompanied by an increase in measurement sensitivity while maintaining linearity for the two developing solutions Example 1 and Example 2.

Procedure for Quantifying ZFD

Several samples are prepared from the solution TEST3 in order to obtain a concentration range between 0 and 100 ppm in the synthetic saline water of sample 2. These samples are assayed by TRF according to 2 methods:

1 mL of each sample is placed in 10-mL flasks in the presence of 9 mL of the Eu-light solution (europium only). After one hour, 2 mL of these new solutions is analysed according to the experimental conditions defined above.

1 mL of each sample is placed in 10-mL flasks in the presence of 9 mL of the solution from Example 2. After one hour, 2 mL of these new solutions is analysed according to the experimental conditions defined above.

Figure 4:
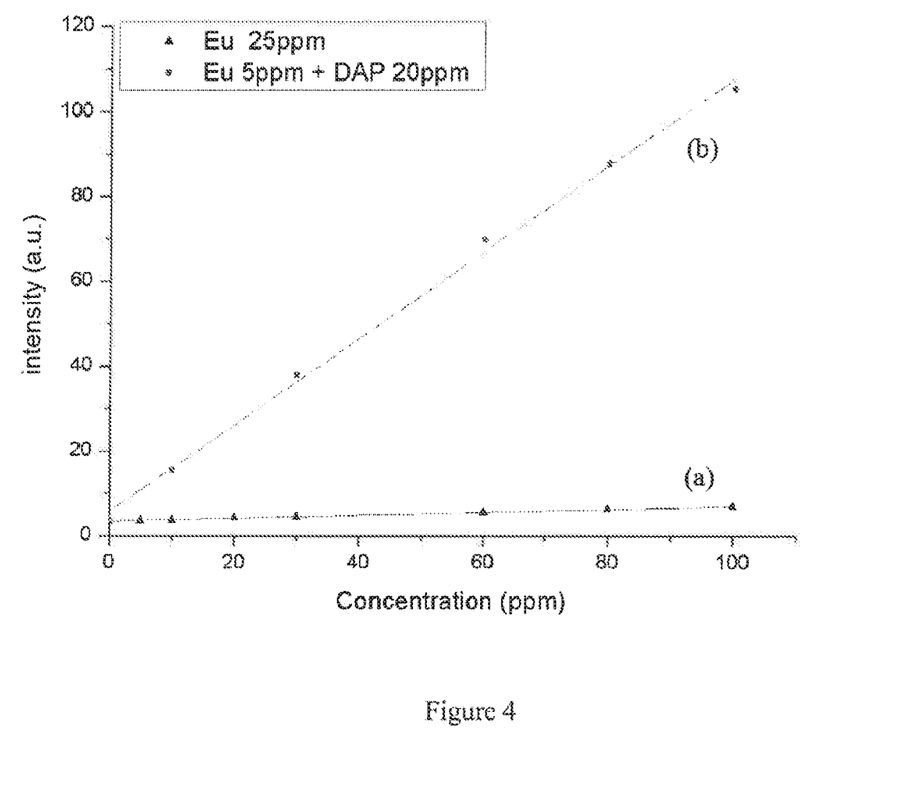
FIG. 4 shows the calibration curves of ZFD with (a) Eu-light ($\lambda_{exc}$=395 nm) and (b) Eu-LD520 ($\lambda_{exc}$=360 nm).

The calibration curves obtained are presented in FIG. 4. When the method is used, the straight lines show an effect of enhancement of the fluorescence accompanied by an increase in measurement sensitivity while maintaining linearity.

II-2 Corrosion Inhibitors

Procedure for Quantifying Nalco EC1621A

Several samples are prepared from the solution TEST4 in order to obtain a concentration range between 0 and 50 ppm in the synthetic saline water of sample 2.

2 mL of each sample is placed in a 10-mL flask in the presence of 8 mL of the solution from Example 3 (Eu-F1510 and Eu-F12510). After one hour, 2 mL of these samples is analysed according to the experimental conditions defined above.

Figure 5:
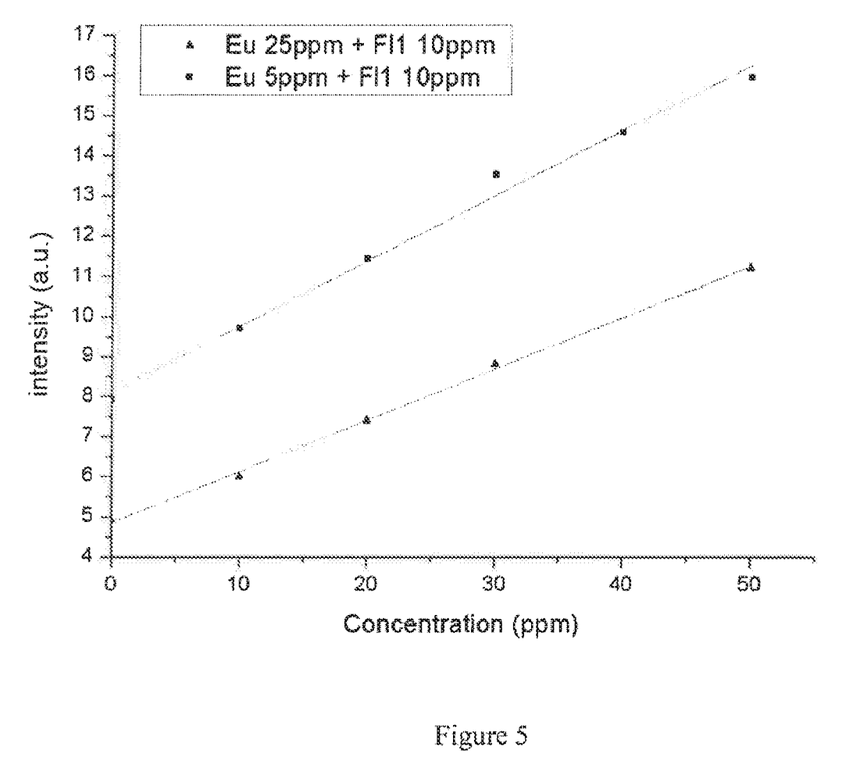
FIG. 5 shows the calibration curves of Nalco EC1621A ($\lambda_{exc}$=350 nm) with (a) Eu-FL510 and (b) Eu-F12510.

The calibration curves obtained are presented in FIG. 5.

Procedure for Quantifying Norust 9711

Several samples are prepared from the solution TEST5 in order to obtain a concentration range between 0 and 100 ppm in the synthetic saline water of sample 2.

2 mL of each sample is placed in a 10-mL flask in the presence of 8 mL of the solution from Example 3 (Eu-F1510). After one hour, 2 mL of this sample is analysed according to the experimental conditions defined above.

Figure 6:
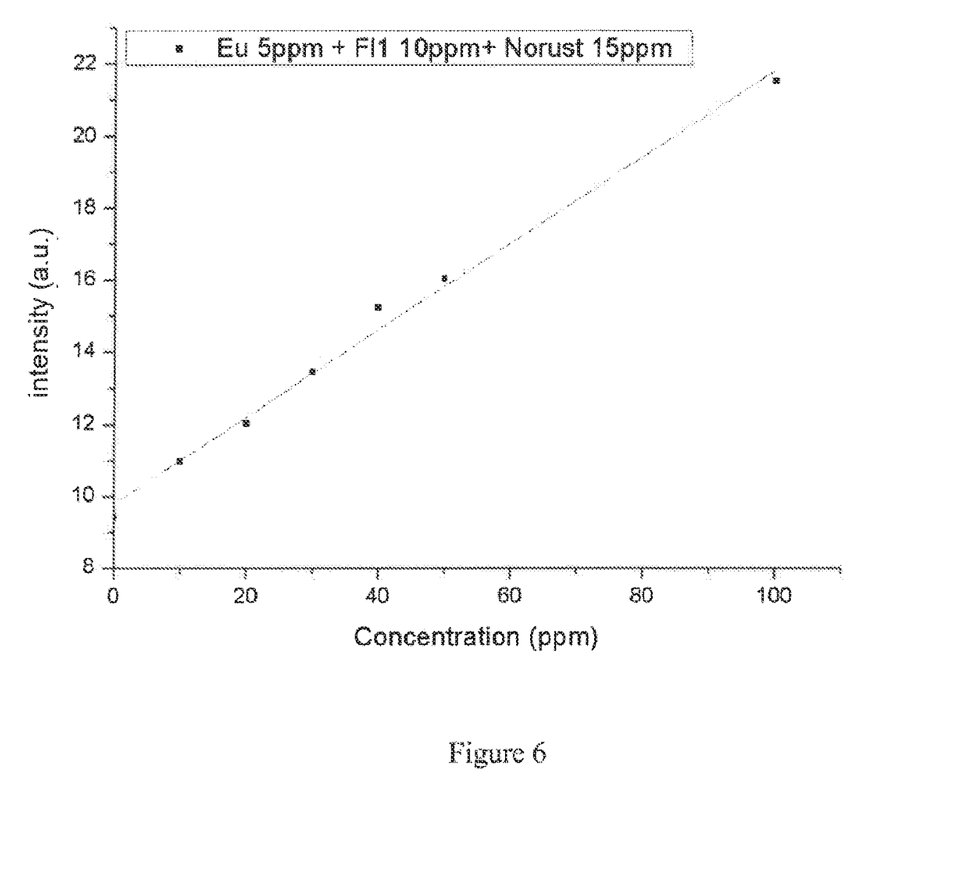
FIG. 6 shows the calibration curves of Norust9711 ($\lambda_{exc}$=350 nm) with Eu-FL510.

The calibration curves obtained are presented in FIG. 6.

III-Effect of the Various Parameters on the Measurement

Interferences of Oil on the Measurement

It is a question of evaluating the influence of oil on the spectral data during quantification of GyptronSA3470.

First a solution with 40 ppm of Gyptron is prepared by diluting the solution TEST1. Finally, approximately 100 ppm of oil is added to this new solution.

1 mL of this sample is placed in a 10-mL flask in the presence of 9 mL of the solution from Example 2 with 100 ppm of europium salt (Eu-LD10020). After one hour, 2 mL of this new solution is analysed according to the experimental conditions defined above. The spectra obtained are presented in FIG. 7.

Figure 7:
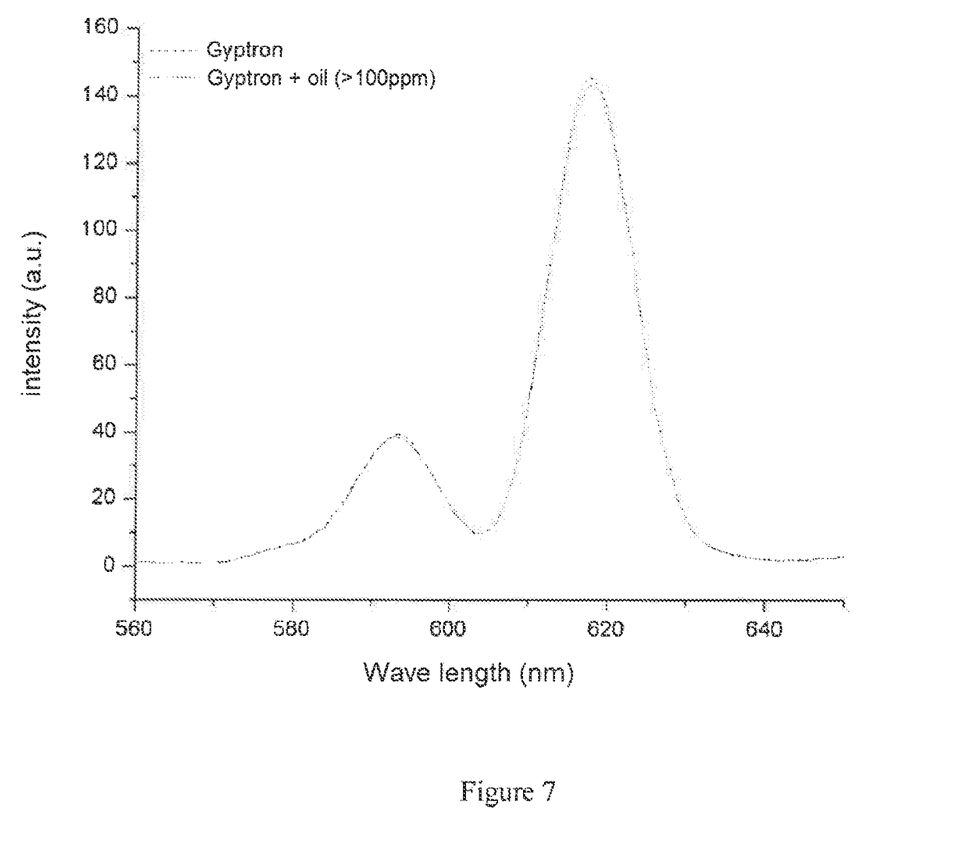
FIG. 7 shows the emission spectra ($\lambda_{exc}$=360 nm) of the Gyptron-Eu complex with and without oil.

The emission spectra show less than 1% variation between the intensities of the signals of the peak of europium at 617 nm.

Influence of Salinity

It is a question of evaluating the influence of the variation in salinity on the spectral data during quantification of GyptronSA3470. Two solutions with 60 ppm of Gyptron are prepared by diluting the solution TEST1 in synthetic sea water (sample 1) with high salinity and synthetic sea water of lower salinity (sample 2).

1 mL of each sample is placed in 10-mL flasks in the presence of 9 mL of the solution from Example 1 with: 5 ppm of europium salt (Eu-LD520) 50 ppm of europium salt (Eu-LD5020) 100 ppm of europium salt (Eu-LD10020)

Figure 8:
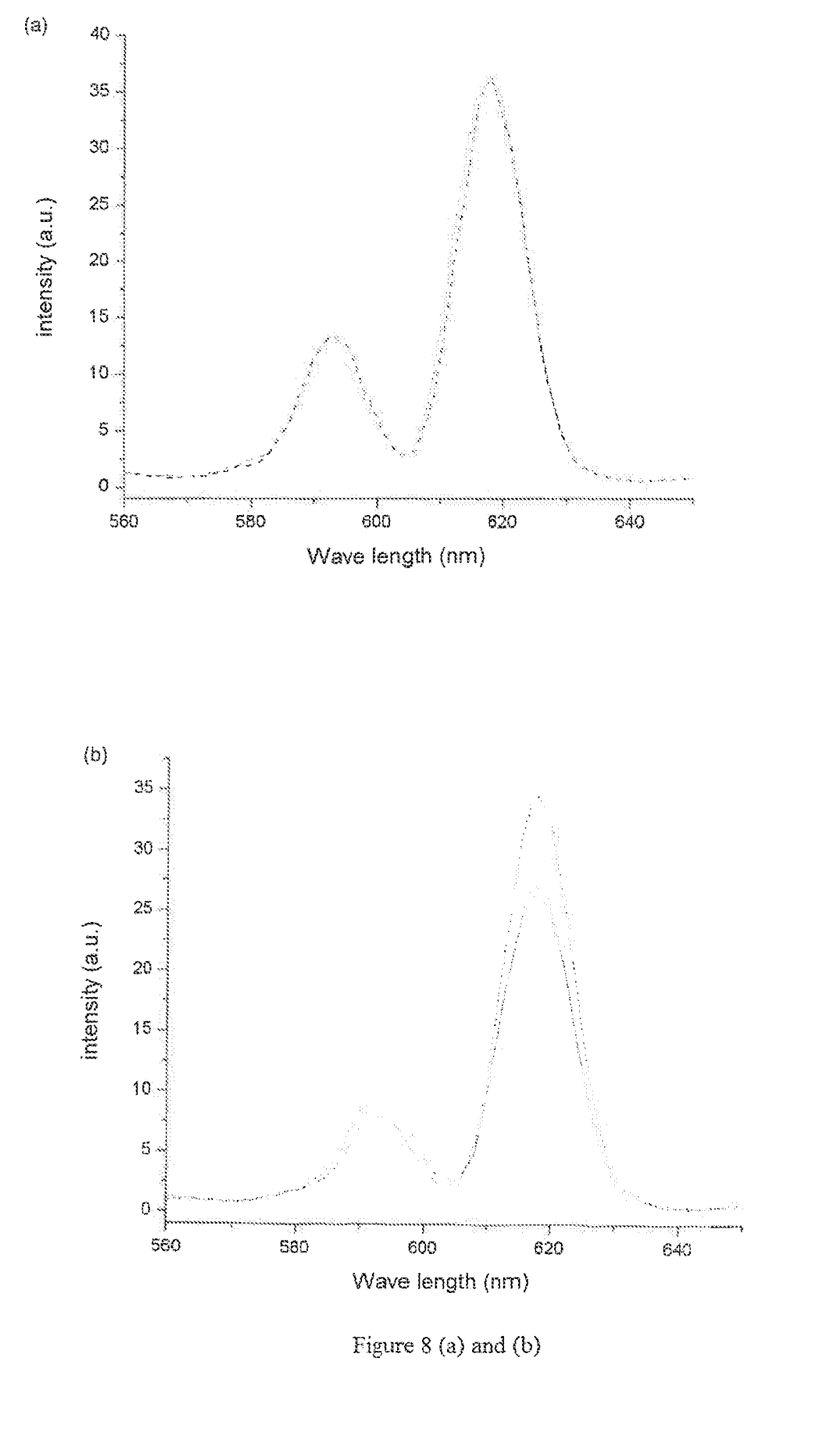
FIG. 8 shows the emission spectra of the Gyptron-Eu complex, quantification with the solution Eu-LD20 at (a) 100 ppm of europium salt (Eu-LD10020), (b) 50 ppm of europium salt (Eu-LD5020) and (c) 5 ppm of europium salt (Eu-LD520) for water of low salinity (dotted curve, sample 1) and water of high salinity (solid curve, sample 2).

After one hour, 2 mL of these new solutions is analysed according to the experimental conditions defined above. The spectra obtained are presented in FIG. 8. The quantity of europium salt in the developing solution Eu-LD20 was adjusted in order to minimize the effect of the salt. In fact, in the presence of a higher concentration of europium ions (from 5 to 100 ppm of salt) the emission signals are similar regardless of the salinity of the medium. However, for a concentration of 5 ppm of europium salt, the difference between the two emission signals (peak at 617 nm) amounts to a difference of 60%.

Influence of Carbonate Ions

It is a question of evaluating the influence of carbonate ions on the spectral data during quantification of F11. First a solution with 50 ppm of F11 is prepared by diluting the solution TEST2. With this new solution, 4 samples are prepared at 0, 1000, 4000 and 7000 ppm of calcium carbonate.

Figure 9:
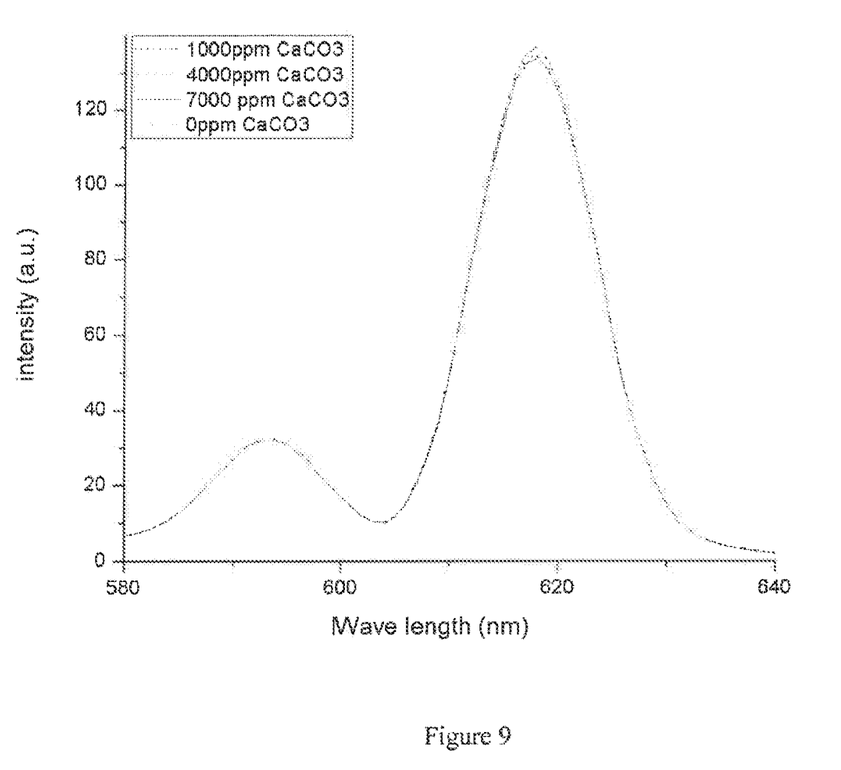
FIG. 9 shows the emission spectra of the F11-Eu complex quantified by the solution Eu-LD10020 in the presence of a variable quantity of $CaCO_3$.

1 mL of each of these samples is placed in 10-mL flasks in the presence of 9 mL of the solution from Example 2 with 100 ppm of europium salt (Eu-LD10020). After one hour, 2 mL of these new solutions is analysed according to the experimental conditions defined above. The spectra obtained are presented in FIG. 9. The emission spectra do not show any effects on the measurement attributable to the carbonates, despite the appearance of a precipitate for the high concentrations of carbonates.

The invention claimed is:

1. Method for detecting additives in an aqueous fluid, comprising:
   a. mixing a developing solution comprising a lanthanide cation and a lanthanide chelating agent, with a sample of the aqueous fluid to be analysed optionally comprising at least one additive, under conditions allowing complexing of the lanthanide by the chelating agent and by the additive that is optionally present,
   b. detecting and, optionally, quantifying the variation in fluorescence associated with the possible presence of the additive in the aqueous fluid by time-resolved fluorescence, wherein the chelating agent is selected from the group consisting of diaminopyridine, imidazoline, hydrolysed poly(maleic anhydride), EDTA, oxalic acid, acetylacetonate, thiodiacetate, nitrilotriacetic acid, or derivatives thereof.

2. Method according to claim 1, wherein the developing solution further comprises at least 1 g/L of chloride ions.

3. Method according to claim 1, wherein the developing solution further comprises at least 1 g/L of a chemical compound used in the production of buffer solution, by 4-(2-hydroxyethyl)-1-piperazine-ethanesulphonic acid (HEPES).

4. Method according to claim 1, wherein a concentration ratio of the chelating agent to the lanthanide cation is between 1:10 and 10:1.

5. Method according to claim 1, wherein the lanthanide cation is selected from: Pr, Nd, Sm, Eu, Tb, Dy, Ho, Er, Tm and Yb, and mixtures thereof.

6. Method according to claim 1, wherein said additive to be detected is present and is an inhibitor of mineral deposits or of corrosion.

7. Method according to claim 6, wherein the inhibitor is of mineral deposits and is selected from:
polyphosphates,
organophosphonates,
polycarboxylic acids,
polymers with a sulphonic acid function, in particular the copolymers of styrenesulphonic acid and maleic acid,
polyphosphinocarboxylic acid (PPCA), optionally sulphonated,
polyethyleneimine (PEI),
silicone polymers functionalized with amine groups, and
copolymers based on quaternary ammonium.

8. Method according to claim 6, wherein the corrosion inhibitor is selected from cyclohexylamine, hexylamine, morpholine, octadecylamine, diethylaminoethanol, the imidazolines and the betaines.

9. Method according to claim 1, wherein an integration delay between excitation of the sample to be analysed and measurement of a signal emitted is between 0.001 and 10 ms.

10. Method according claim 2, wherein the concentration of chloride ions is between 10 and 50 g/L.

11. Method according to claim 4, wherein the concentration ratio is between 1:3 and 3:1.

12. Method according to claim 5, wherein the lanthanide cation is Eu.

13. Method according to claim 9, wherein the integration delay between excitation of the sample to be analysed and measurement of the signal emitted is between 0.01 and 5 ms.

14. Method according to claim 9, wherein the integration delay between excitation of the sample to be analysed and measurement of the signal emitted is between 0.1 and 3 ms.

15. Method according to claim 1, wherein said additive to be detected is present and does not have intrinsic fluorescence.

16. Method according to claim 1, wherein the aqueous fluid is an extract of a petroleum fluid containing water.

* * * * *